United States Patent
Sgroi et al.

(10) Patent No.: US 11,078,538 B2
(45) Date of Patent: Aug. 3, 2021

(54) POST-TREATMENT BREAST CANCER PROGNOSIS

(71) Applicants: Biotheranostics, Inc., San Diego, CA (US); The General Hospital Corporation, Boston, MA (US)

(72) Inventors: Dennis Sgroi, Cambridge, MA (US); Mark G. Erlander, Carlsbad, CA (US); Yi Zhang, San Diego, CA (US); Catherine A. Schnabel, San Diego, CA (US)

(73) Assignee: Biotheranostics, Inc., San Diego, CA (US)

(*) Notice: Subject to any disclaimer, the term of this patent is extended or adjusted under 35 U.S.C. 154(b) by 35 days.

(21) Appl. No.: 15/298,128

(22) Filed: Oct. 19, 2016

(65) Prior Publication Data

US 2017/0253931 A1    Sep. 7, 2017

Related U.S. Application Data

(63) Continuation of application No. 13/914,617, filed on Jun. 10, 2013, now abandoned, which is a continuation of application No. PCT/US2011/064290, filed on Dec. 9, 2011.

(60) Provisional application No. 61/421,627, filed on Dec. 9, 2010.

(51) Int. Cl.
*A61K 39/00* (2006.01)
*C12Q 1/6886* (2018.01)

(52) U.S. Cl.
CPC ..... *C12Q 1/6886* (2013.01); *C12Q 2600/106* (2013.01); *C12Q 2600/118* (2013.01); *C12Q 2600/158* (2013.01)

(58) Field of Classification Search
CPC ............ C12Q 1/6886; C12Q 2600/118; C12Q 2600/158; A61P 35/00
See application file for complete search history.

(56) References Cited

U.S. PATENT DOCUMENTS

| | | | |
|---|---|---|---|
| 4,981,783 | A | 1/1991 | Augenlicht |
| 6,291,170 | B1 | 9/2001 | Van Gelder et al. |
| 6,328,709 | B1 | 12/2001 | Hung et al. |
| 6,482,600 | B1 | 11/2002 | Burner et al. |
| 6,642,009 | B2 | 11/2003 | Hung |
| 6,673,024 | B2 | 1/2004 | Soito et al. |
| 6,794,141 | B2 | 9/2004 | Erlander et al. |
| 7,504,214 | B2 | 3/2009 | Erlander et al. |
| 7,514,209 | B2 | 4/2009 | Dai et al. |
| 7,930,105 | B2 | 4/2011 | Erlander et al. |
| 9,447,470 | B2 | 9/2016 | Erlander et al. |
| 2001/0039015 | A1 | 11/2001 | Sauter |
| 2002/0044941 | A1 | 4/2002 | Rosen et al. |
| 2002/0102265 | A1 | 8/2002 | Hong et al. |
| 2003/0049701 | A1 | 3/2003 | Muraca |
| 2003/0087270 | A1 | 5/2003 | Schlegel et al. |
| 2003/0124128 | A1 | 7/2003 | Lillie et al. |
| 2003/0138833 | A1 | 7/2003 | Polyak et al. |
| 2003/0219760 | A1 | 11/2003 | Gordon et al. |
| 2005/0079518 | A1 | 4/2005 | Baker et al. |
| 2005/0239079 | A1 | 10/2005 | Erlander et al. |
| 2005/0239083 | A1 | 10/2005 | Erlander et al. |
| 2006/0154267 | A1 | 7/2006 | Ma et al. |
| 2011/0136680 | A1 | 6/2011 | Erlander et al. |
| 2013/0281502 | A1 | 10/2013 | Sgroi et al. |

FOREIGN PATENT DOCUMENTS

| | | | |
|---|---|---|---|
| EP | 2333119 A1 | | 6/2011 |
| WO | WO 2002/103320 A2 | | 12/2002 |
| WO | WO 2003/060470 A2 | | 7/2003 |
| WO | WO 2005/008213 A2 | | 1/2005 |
| WO | WO 2006/004600 A1 | | 1/2006 |
| WO | WO 2006/119593 A1 | | 11/2006 |
| WO | WO 2006/132971 A2 | | 12/2006 |
| WO | WO 2009/108215 A1 | | 9/2009 |
| WO | WO2009108215 | * | 9/2009 |
| WO | WO 2012/079059 A2 | | 6/2012 |
| WO | WO 2012/079059 A3 | | 6/2012 |
| WO | WO 2013/070521 A1 | | 5/2013 |

(Continued)

OTHER PUBLICATIONS

Ma et al Clin Cancer Res, 14:26-1-08, 2008, IDS #C10, filed on Jun. 21, 2017 (Year: 2008).*
Big 1-98 Collaborative Group et al., "Letrozole therapy alone or in sequence with tamoxifen in women with breast cancer," *N. Engl. J. Med.*,361(8):766-776 (2009).
Cianfrocca et al., "Prognostic and predictive factors in early-stage breast cancer," *Oncologist*, 9(6):606-616 (2004).
Desmedt et al., "Proliferation: the most prominent predictor of clinical outcome in breast cancer," *Cell Cycle*, 5(19):2198-2202 (2006).

(Continued)

*Primary Examiner* — Lei Yao
(74) *Attorney, Agent, or Firm* — Jones Day

(57) ABSTRACT

The disclosure includes the identification and use of gene expression profiles, or patterns, with clinical relevance to extended treatment and cancer-free survival in a patient. In particular, the disclosure includes the identities of genes that are expressed in correlation with benefit in a switch in endocrine therapy used to treat a patient. The levels of gene expression are disclosed as a molecular index for predicting clinical outcome, and so prognosis, for the patient. The disclosure further includes methods for predicting cancer recurrence, and/or predicting occurrence of metastatic cancer, after initial treatment with an anti-estrogen agent. The disclosure further includes methods for determining or selecting the treatment of a subject based upon the likelihood of life expectancy, cancer recurrence, and/or cancer metastasis.

15 Claims, No Drawings

(56) References Cited

FOREIGN PATENT DOCUMENTS

| WO | WO 2015/038682 A1 | 3/2015 |
| WO | WO 2015/184182 A1 | 12/2015 |

OTHER PUBLICATIONS

Goetz et al., "A two-gene expression ratio of homeobox 13 and interleukin-17B receptor for prediction of recurrence and survival in women receiving adjuvant tamoxifen," Clin. Cancer Res., 12(7 Pt 1):2080-2087 (2006).
Goldhirsch et al., "Meeting highlights: international expert consensus on the primary therapy of early breast cancer 2005," Ann. Oncol., 16(10):1569-1583 (2005).
Hirose et al., "MgcRacGAP is involved in cytokinesis through associating with mitotic spindle and midbody," J. Biol. Chem. ,276(8):5821-5828 (2001).
Jerevall et al., "Exploring the two-gene ratio in breast cancer—independent roles for HOXB13 and IL17BR in prediction of clinical outcome," Breast Cancer Res. Treat., 107(2):225-234 (2008).
Jerevall et al., "Predictive relevance of HOXB13 protein expression for tamoxifen benefit in breast cancer," Breast Cancer Res., 12(4):R53 (2010).
Loi et al., "Definition of clinically distinct molecular subtypes in estrogen receptor-positive breast carcinomas through genomic grade," J. Clin. Oncol., 25(10):1239-1246 (2007).
Ma et al., "A five-gene molecular grade index and HOXB13:IL17BR are complementary prognostic factors in early stage breast cancer," Clin. Cancer Res., 14(9):2601-2608 (2008).
Ma et al., "A two-gene expression ratio predicts clinical outcome in breast cancer patients treated with tamoxifen," Cancer Cell., 5(6):607-616 (2004).
Ma et al., "Gene expression profiles of human breast cancer progression," Proc. Natl. Acad Sci. USA,100(10):5974-5979 (2003).
Ma et al., "The HOXB13:IL17BR expression index is a prognostic factor in early-stage breast cancer," J. Clin. Oncol., 24(28):4611-4619 (2006).
Miller et al., "An expression signature for p53 status in human breast cancer predicts mutation status, transcriptional effects, and patient survival," Proc. Natl. Acad. Sci. USA, 102(38):13550-13555 (2005).
Paik et al., "A multigene assay to predict recurrence of tamoxifen-treated, node-negative breast cancer," N. Engl. J. Med., 351(27):2817-2826 (2004).
Pawitan et al., "Gene expression profiling spares early breast cancer patients from adjuvant therapy: derived and validated in two population-based cohorts," Breast Cancer Res., 7(6):R953-R964 (2005).
Rundle et al., "Design options for molecular epidemiology research within cohort studies," Cancer Epidemiol Biomarkers Prev., 14(8)1899-1907 (2005).
Sgroi et al., "Prediction of late disease recurrence and extended adjuvant letrozole benefit by the HOXB13/IL17BR biomarker," JNCI, 105(14):1036-1042 (2013).
Sotiriou et al., "Gene expression profiling in breast cancer: understanding the molecular basis of histologic grade to improve prognosis," J. Nat. Cancer Inst., 98(4):262-272 (2006).
Sotiriou et al., "Taking gene-expression profiling to the clinic: when will molecular signatures become relevant to patient care?," Nat. Rev. Cancer, 7(7):545-553 (2007).
Van 'T Veer et al., "Gene expression profiling predicts clinical outcome of breast cancer," Nature, 415(6871):530-536 (2002).
Whitfield et al., "Identification of genes periodically expressed in the human cell cycle and their expression in tumors," Mol. Biol. Cell., 13(6):1977-2000 (2002).
Abramovitz et al., "A systems approach to clinical oncology: focus on breast cancer," Proteome Sci., 4:5 (2006).
Alizadeh et al., "Distinct types of diffuse large B-cell lymphoma identified by gene expression profiling," Nature, 403(6769):503-511 (2000).
Ansfield et al., "A ten-year study of 5-flurouracil in disseminated breast cancer with clinical results and survival times," Cancer Res., 29(5):1062-1066 (1969).
Bardou et al., "Progesterone receptor status significantly improves outcome prediction over estrogen receptor status alone for adjuvant endocrine therapy in two large breast cancer databases," J. Clin. Oncol., 21(10):1973-1979 (2003).
Becker et al., "Distinct gene expression patterns in a tamoxifen-sensitive human mammary carcinoma xenograft and its tamoxifen-resistant subline MaCa 3366/TAM," Mol. Cancer Ther., 4(1):151-168 (2005).
Benner et al., "Evolution, language and analogy in functional genomics," Trends Genetics, 17(7):414-418 (2001).
Bepler et al., "RRM1 and PTEN as prognostic parameters for overall and disease-free survival in patients with non-small-cell lung cancer," J. Clin. Oncol., 22(10):1878-1885 (2004).
Betsil et al., "Intraductal carcinoma. Long-term follow-up after treatment by biopsy alone," JAMA, 239(18):1863-1867 (1978).
Bissett et al., "Human papillomavirus genotype detection and viral load in paired genital and urine samples from both females and males," J. Med. Virol., 83:1744-1751 (2011).
Bittner et al., "Molecular classification of cutaneous malignant melanoma by gene expression profiling," Nature, 406(6795):536-540 (2000).
Bonner et al., "Laser caputre microdissection: molecular analysis of tissue," Science, 278(5342):1481-1483 (1997).
Brown et al., "Knowledge based analysis of microarray gene expression data by using support vector machines," Proc. Natl. Acad. Sci. USA,97(1):262-267 (2000).
Bruggemeier et al., "Aromatase inhibitors in the treatment of breast cancer," Endocrine Rev., 26(3):331-345 (2005).
Buzdar, "Anastrozole: a new addition to the armamentarium against advanced breast cancer," Am. J. Clin. Oncol., 21(2):161-166 (1998).
Chen et al., "BRCA1, BRCA2, and Rad51 operate in a common DNA damage response pathway," Cancer Res., 59(7 Suppl):1752s-1756s (1999).
Chen et al., "Discordant protein and mRNA expression in lung adenocarcinomas," Mol. Cell. Proteomics, 1:304-313 (2002).
Chen et al., "Inhibition of human cancer cell growth by inducible expression of human ribonucleotide reductase antisense cDNA," Antisense Nucleic Acid Drug Dev., 10(2):111-116 (2000).
Chng et al., "A gene expression based centrosome index is a powerful prognostic factor in myeloma," Blood, 108: Abstract 3388 (2006).
Clarke et al., "Antiestrogen resistance in breast cancer and the role of estrogen receptor signaling," Oncogene, 22:7316-7339 (2003).
Collins et al., "The application of genomic and proteomic technologies in predictive, preventive and personalized medicine," Vascul. Pharmacol., 45(5):258-267 (2006).
Cornfield et al., "The prognostic significance of multiple morphologic features and biologic markers in ductal carcinoma in situ of the breast: a study of a large cohort of patients treated with surgery alone," Cancer, 100(11):2317-2327 (2004).
Cronin et al., "Measurement of gene expression in archival paraffin-embedded tissues: development and performance of a 92-gene reverse transcriptase-polymerase chain reaction assay," Am. J. Pathol. ,164(1):35-42 (2004).
Cuzick et al., "Effect of anastrozole and tamoxifen as adjuvant treatment for early-stage breast cancer; 10-year analysis of the ATAC trial," Lancet Oncol., 11:1135-1142 (2010).
Cuzick et al., "Prognostic value of a cominded estrogen receptor, progestrone receptor, Ki-67, and human epidermal growth factor receptor 2 immunohistochemcial score and comparison with the genomic health recurrence score in early breast cancer," J. Clin. Oncol., 29(32):4273-4278 (2011).
Dabholkar et al., "Messenger RNA levels of XPAC and ERCC1 in ovarian cancer tissue correlate with response to platinum-based chemotherapy," J. Clin. Invest., 94:703-708 (1994).
Daidone et al., "Biomarkers and outcome after tamoxifen treatment in node-positive breast cancers from elderly women," Br. J. Cancer, 82(2):270-277 (2000).
Dalgin et al., "Portraits of breast cancer progression," BMC Bioinformatics, 8(291):1-16 (2007).

(56) References Cited

OTHER PUBLICATIONS

Dalton et al., "Histologic grading of breast cancer: linkage of patient outcome with level of pathologist agreement," *Mod. Pathol.*, 13(7):730-735 (2000).
Dauvois et al., "Antiestrogen ICI 164,384 reduces cellular estrogen receptor content by increasing its turnover," *Proc. Natl. Acad. Sci. USA*, 89:4037-4041 (1992).
De Vos et al., "Gene expression profile of serial samples of transformed B-cell lymphomas," *Lab. Invest.*, 83(2):271-285 (2003).
Derisi et al., "Use of a cDNA microarray to analyse gene expression patterns in human cancer," *Nat. Genet.*,14(4):457-460 (1996).
Desmedt et al., "Strong time dependence of the 76-gene prognostic signature for node-negative breast cancer patients in the TRANSBIG multicenter independent validation series," *Clin. Cancer Res.*, 13(11):3207-3214 (2007).
Dowsett et al., "Prediction of risk of distant recurrence using the 21-gene recurrence score in node-negative and node-ositive postmenopausal patients with breast cancer treated with anastrozole or tamoxifen; a transATAC study," *J. Clin. Oncol.*, 28(11):1829-1834 (2010).
Dowsett, "Overexpression of HER-2 as a resistance mechanism to hormonal therapy for breast cancer," *Endocr. Relat. Cancer*, 8(3):191-195 (2001).
Draghici et al., "A systems biology approach for pathway level analysis," *Genome Res.*, 17:1537-1545 (2007).
Dupont et al., "Risk factors for breast cancer in women with proliferative breast disease," *N. Engl. J. Med.*,312(3):146-151 (1985).
Dutertre et al., "Molecular mechanisms of selective estrogen receptor modulator (SERM) action," *J. Pharmacol. Exper. Ther.*, 295(2):431-437 (2000).
Ellis et al., "Letrozole is more effective neoadjuvant endocrine therapy than tamoxifen for ErbB-1- and/or ErbB-2-positive, estrogen receptor-positive primary breast cancer: evidence from a phase III randomized trial," *J. Clin. Oncol.*, 19(18):3808-3816 (2001).
Ellis et al., "Neoadjuvant comparisons of aromatase inhibitors and tamoxifen: pretreatment determinants of response and on-treatment effect," *J. Steroid Biochem. Mol. Biol.*, 86:301-307 (2003).
Elston et al., "Pathological prognostic factors in breast cancer. I. The value of histological grade in breast cancer: experience from a large study with long-term follow-up," *Histopathology*, 19(5):403-410 (1991).
Ester et al., "Imparied BUB1B mRNA expression is associated with osteogenic sarcoma," *Proc. Am. Assoc. Cancer Res.*, 46:1052, abstract 4448 (2005).
Fabian et al., "Short-term breast cancer prediction by random periareolar fine-needle aspriation cytology and the gail risk model," *J. Natl. Cancer Inst.*, 92(15):1217-1227 (2000).
Feng et al., "Molecuar biomarkers for cancer detection in blood and bodily fluids," *Crit. Rev. Clin. Lab. Sci.*, 43(5-6):497-560 (2006).
Fernandez et al., "Quantitative oestrogen and progeseterone receptor values in primary breast cancer and predictability of response to endocrine therapy," *Clin. Oncol.*, 9:245-250 (1983).
Fernö et al., "Results of two or five years of adjuvant tamoxifen correlated to steroid receptor and S-phase levels," *Breast Cancer Res. Treat.*, 59:69-76 (2000).
Fitzgibbons et al., "Prognostic factors in breast cancer. College of American Pathologists Consensus Statement 1999," *Arch. Pathol. Lab. Med.*, 124(7):966-978 (2000).
Fraser et al., "Columnar alteration with prominent apical snouts and secretions: a spectrum of changes frequently present in breast biopsies performed for microcalcifications," *Am. J. Surg. Pathol.*, 22(12):1521-1527 (1998).
Furey et al., "Support vector machine classification and validation of cancer tissue samples using microarray expression data," *Bioinformatics*, 16(10):906-914 (2000).
Galaktionov et al., "CDC25 phosphatases as potential human oncogenes," *Science*, 269(5230):1575-1577 (1995).
Garber et al., "Diversity of gene expression in adenocarcinoma of the lung," *Proc. Natl. Acad. Sci. USA*, 98(24):13784-13789 (2001).
Gelmini et al., "Quantitative polymerase chain reaction-based homogeneous assay with fluorogenic probes to measure c-erbB-2 oncogene amplification," *Clin. Chem.*, 43(5):752-758 (1997).
Genbank Accession No. AA454563.1, Jun. 6, 1997.B58.
Gianni et al., "Feasibility and tolerability of sequential doxorubicin/paclitaxel followed by cyclophosphamide, methotrexate, and fluorouracil and its effects on tumor response as preoperative therapy," *Clin. Cancer Res.*, 11(24 Pt 1):8715-8721 (2005).
Gibson et al., "A novel method for real time quantitative RT-PCR," *Genome Res.*, 6:995-1001 (1996).
Ginzinger, "Gene quantification using real-time quantitative PCR: an emerging technology hits the mainstream, " *Exp. Hematol.*, 30:503-512 (2002).
Golpon et al., "HOX genes in human lung. Altered expression in primary pulmonary hypertension and emphysema," *Am. J. Pathol.*, 158(3):955-966 (2001).
Golub et al., "Molecular classification of cancer: class discovery and class prediction by gene expression monitoring," *Science*, 286(5439):531-537 (1999).
Gonzalez-Angulo et al."Future of personalized medicine in oncology: a systems biology approach," *J. Clin. Oncol.*, 28(16):2777-2783 (2010).
Goss et al., "A randomized trial of letrozole in postmenopausal women after five years of tamoxifen therapy for early-stage breast cancer," *N. Engl. J. Med.*, 349(19):1793-1802 (2003).
Goss et al., "Randomized Trial of Letrozole Following Tamoxifen as Extended Adjuvant Therapy in Receptor-Positive Breast Cancer: Updated Findings from NCIC CTG MA.17," *J. Natl. Cancer Inst.*, 97(17):1262-1271 (2005).
Gruvberger et al., "Estrogen receptor status in breast cancer is associated with remarkably distinct gene expression patterns," *Cancer Res.*, 61(16):5979-5984 (2001).
Habel et al., "HOXB13:IL17BR and molecular grade index and risk of breast cancer death among patients with lymph node-negative invasive disease," *Breast Cancer Res.*,15:R24 (2013).
Hall et al., "The multifaceted mechanisms of estradiol and estrogen receptor signaling," *J. Biol. Chem.*, 276(40):36869-36872 (2001).
Hartmann et al., "Benign breast disease and the risk of breast cancer," *N. Engl. J. Med.*, 353(3):229-237 (2005).
Hedenfalk et al., "Gene-expression profiles in hereditary breast cancer," *N. Engl. J. Med.*, 344(8):539-548 (2001).
Herschkowitz et al., "Identification of conserved gene expression features between murine mammary carcinoma models and human breast turmors," *Genome Biol.*, 8:R76 (2007).
Hilsenbeck et al., "Statistical analysis of array expression data as applied to the problem of tamoxifen resistance," *J. Natl. Cancer Inst.*, 91(5):453-459 (1999).
Holland et al., "Ductal carcinoma in situ: a proposal for a new classification," *Semin. Diang. Pathol.*, 11(3):167-180 (1994).
Howell et al., "Where do selective estrogen receptor modulators (SERMs) and aromatase inhibitors (AIs) now fit into breast cancer treatment algorithms?," *J. Steroid Biochem. Mol. Biol.*, 79(1-5):227-237 (2001).
Howell et al., "The use of selective estrogen receptor modulators and selective estrogen receptor down-regulators in breast cancer," *Best Pract. Res. Clin. Endocrinol Metab.*, 18(1):47-66 (2004).
Huang et al., "Gene expression predictors of breast cancer outcomes," *Lancet*, 361:1590-1596 (2003).
Ivshina et al., "Genetic reclassification of histologic grade delineates new clinical subtypes of breast cancer," *Cancer Res.*, 66(21):10292-10301 (2006).
Jansen et al., "HOXB13-to-IL17BR expression ratio is related with tumor aggressiveness and response to tamoxifen of recurrent breast cancer: a retrospective study," *J. Clin. Oncol.*, 25(6):662-668 (2007).
Jordan et al, "Historical perspective on hormonal therapy of advanced breast cancer," *Clin. Ther.*, 24(Suppl. A):A3-A16 (2002).
Jordan et al., "Introducing a new section to breast cancer research: endocrinology and hormone therapy," *Breast Cancer Res.*, 5:281-283 (2003).
Kato et al., "Expression of survivin in esophageal cancer: correlation with the prognosis and response to chemotherapy," *Int. J. Cancer (Pred. Oncol.)*, 95:92-95 (2001).

(56) References Cited

OTHER PUBLICATIONS

Korkaya et al., "Regulation of mammary stem/progenitor cells by PTEN/Akt/β-catenin signaling," *PLoS Biology*, 7(6):e100121 (2009).
Lennon et al., "The I.M.A.G.E. Consortium: an integrated molecular analysis of genomes and their expression," *Genomics*, 33(1):151-152 (1996).
Levenson et al., "Gene expression profiles with activation of the estrogen receptor α-selective estrogen receptor modulator complex in breast cancer cells expressing wild-type estrogen receptor," *Cancer Res.*, 62:4419-4426 (2002).
Lewis et al., "Molecular classification of melanoma using real-time quantitative reverse transcriptase-polymerase chain reaction," *Cancer*, 104(8):1678-1686 (2005).
Lingle et al., "Centrosome amplification drives chromosomal instability in breast tumor development," *Proc. Natl. Acad. Sci. USA*, 99(4):1978-1983 (2002).
Lu et al., "SSelection of potential markers for epithelial ovarian cancer with gene expression arrays and recursive descent partition analysis.," *Clin. Cancer Res.*, 10:3291-3300 (2004).
Lucentini et al., "Gene association studies typically wrong," *The Scientist*, 18(24):20 (2004).
Luo et al., "Gene expression profiles of laser-captured adjacent neuronal subtypes," *Nat. Med.*, 5(1):117-122 (1999).
Luo et al., "Higher expression of human kallikrein 10 in breast cancer tissue predicts tamoxifen resistance," *Br. J. Cancer*, 86:1790-1796 (2002).
Ma et al., "HOXB13 may predict response to neoadjuvant letrozole in patients with estrogen receptor-positive breast cancer," Novartis poster, retrieved from the Internet: URL:http://www.biotheranostics.com/wp-content/uploads/Novartis-BTX_SABCS_2009.pdf, retrieved on Dec. 17, 2014, Abstract only.
Maacke et al., "Over-expression of wild-type Rad51 correlates with histological grading of invasive ductal breast cancer," *Int. J. Cancer*, 88(6):907-913 (2000).
Mark et al., "HER-2/neu gene amplification in stages I-IV breast cancer detected by fluorescent in situ hybridization," *Genet. Med.*, 1(3):98-103 (1999).
Marshall et al., "Risk of breast cancer associated with tatypical hyperplasia of lobular and ductal types," *Cancer Epidemiol Biomarkers Prev.*, 6(5):297-301 (1997).
May, "How many species are there on earth?," *Science*, 241:1441-1449 (1988).
Mello-Grand eta l., "Gene expression profiling and prediction of response to hormonal neoadjuvant treatment with anastrozole in surgically resectable breast cancer," *Breast Cancer Res. Treat.*, 121:399-411 (2010).
Miller et al., "Gene expression profiles differentiating between breast cancers clinically responsive or resistant to letrozole," *J. Clin. Oncol.*, 27(9):1382-1387 (2009).
Nardelli et al., "Estrogen and progesterone receptors status in the prediction of response of breast cancer to endocrine therapy," *Eur. J. Gynaec. Oncol.*, 3:151-158 (1986).
Nicholson et al., "Epidermal growth factor receptor in breast cnacer: association with response to endocrine therapy," *Breast Cancer Res. Treat.*, 29:117-125 (1994).
O'Driscoll et al., "Multiple drug resistance-related messenger RNA expression in archival formalin-fixed paraffin-embedded human breast tumour tissue," *Eur. J. Cancer*, 32A(1):128-133 (1996).
Okuda et al., "Epigenetic inactivation of the candidate tumor suppressor gene HOXB13 in human real cell carcinoma," *Oncogene*, 25:1733-1742 (2006).
Osborne et al., "Growth factor receptor cross-talk with estrogen receptor as a mechanism for tamoxifen resistance in breast cancer," *The Breast*, 12:362-367 (2003).
Osborne et al., "The value of estrogen and progesterone receptors in the treatment of breast cancer," *Cancer*, 46:2884-2888 (1980).
Oyama et al., "Atypical cystic lobules: an early stage in the formation of low-grade ductal carcinoma in situ," *Virchows Arch.*, 435(4):413-421 (1999).
Page et al., "Combined histologic and cytologic criteria for the diagnosis of mammary atypical ductal hyperplasia," *Hum. Pathol.*, 23(10):1095-1097 (1992).
Page et al., "Intraductal carcinoma of the breast: follow-up after biopsy only," *Cancer*, 49(4):751-758 (1982).
Page et al., "Prediction of node-negative breast cancer outcome by histologic grading and S-phase analysis by flow cytometry: an Eastern Cooperative Oncology Group Study (2192)," *Am. J. Clin. Oncol.*, 24(1):10-18 (2001).
Paik, "Molecular profiling of breast cancer," *Breast Cancer*, 18:59-63 (2006).
Pepe et al., "An interpretation for the ROC curve and inference using GLM procedures," *Biometrics*, 56(2):352-359 (2000).
Perou et al., "Distinctive gene expression patterns in human mammary epithelial cells and breast cancers," *Proc. Natl. Acad. Sci. USA*,96(16):9212-9217 (1999).
Perou et al., "Molecular portraits of human breast tumours," *Nature*, 406(6797):747-752 (2000).
Ramaswamy et al., "A molecular signature of metastasis in primary solid tumors," *Nat. Genet.*, 33(1):49-54 (2003).
Romond et al., "Trastuzumab plus adjuvant chemotherapy for operable HER2-positive breast cancer," *N. Engl. J. Med.*, 353(16):1673-1684 (2005).
Salonga et al., "Colorectal tumors responding to 5-fluorouracil have low gene expression levels of dihydropyrimidine dehydrogenase, thymidylate synthase, and thymidine phosphorylase," *Clin. Cancer Res.*, 6:1322-1327 (2000).
Scintu et al., "Genomic instability and increased expression of BUB1B and MAD2L1 genes in ductal breast carcinoma," *Cancer Letters*, 254:298-307 (2007).
Sengar et al., "The EH and SH3 domain Ese proteins regulate endocytosis by linking to dynamin and Eps15," *EMBO J.*, 18(4):1159-1171 (1999).
Sgroi et al., "In vivo gene expression profile analysis of human breast cancer progression," *Cancer Res.*, 59(22):5656-5661 (1999).
Shah et al., "HOXB13 mediates tamoxifen resistance and invasiveness in human breast cancer by suppressing ERα and inducing IL-6 expression," *Cancer Res.*, 73(17):5449-5458 (2013).
Sheridan et al., "Control of TRAIL-induced apoptosis by a family of signaling and decoy receptors," *Science*, 277(5327):818-821 (1997).
Shi et al., "A novel cytokine receptor-ligand pair," *J. Biol. Chem.*, 2;75(25):19167-19176 (2000).
Shou et al., "Mechanisms of tamoxifen resistance: increased estrogen receptor-HER2/neu cross-talk in ER/HER2-positive breast cancer," *J. Natl. Cancer Inst.*, 96(12):926-935 (2004).
Singletary et al., "Revision of the American joint committee on cancer staging system for breast cancer," *J. Clin. Oncol.*, 20(17):3628-3636 (2002).
Sørlie et al., "Gene expression patterns of breast carcinomas distinguish tumor subclasses with clinical implications," *Proc. Natl. Acad. Sci. USA*, 98(19):10869-10874 (2001).
Sørlie et al., "Repeated observation of breast tumor subtypes in independent gene expression data sets," *Proc. Natl. Acad. Sci. USA*, 100(14):8418-8423 (2003).
Sotiriou et al., "Breast cancer classification and prognosis based on gene expression profiles from a population-based study," *Proc. Natl. Acad. Sci. USA*, 100(18):10393-10398 (2003).
Sotiriou et al., "Gene expression profiles derived from fine needle aspiration correlate with response to systemic chemotherapy in breast cancer," *Breast Cancer Res.*, 4:R3 (2002).
Sotiriou et al., "Gene expression profiling in breast cancer: understanding the molecular basis of histologic grade to improve prognosis," *J. Nat. Cancer Inst.*,98(4) Supplemental Data (2006).
Srinivas eta l., "Trends in biomarker research for cancer detection," *Lancet Oncol.*, 2:698-704 (2001).
Strauss et al., "Detection and typing of human papillomavirus DNA in paired urine and cervical scrapes," *Eur. J. Epidermiol*, 15(6):537-543 (1999).
Tan-Chiu et al., "Effects fo tamoxifen on benign breast disease in women at high risk for breast cancer," *J. Natl. Cancer Inst.*, 95(4):302-307 (2003).

(56) References Cited

OTHER PUBLICATIONS

Tarca et al., "A novel signaling pathway impact analysis," *Bioinformatics*, 25:75-82 (2009).
Thomas et al., "The Elf group of Ets-related transcription factors ELF3 and ELF5," *Adv. Exper. Med. Biol.*, 480:123-128 (2000).
Turner et al., "Adjuvant chemotherapy: Which patient? What regimgen?," ASCO University, 2013 ASCO Educational Book, [Retrieved on Aug. 17, 2015]. Online ebook. Retrieved from the Internet: <URL:http://meetinglibrary.asco.org/contenU145-132> 5 pages (2013).
Unger et al., "Characterization of adjacent breast tumors using oligonucleotide microarrays," *Breast Cancer Res.*, 3(5):336-341 (2001).
Van De Vijver et al., "A gene-expression signature as a predictor of survival in breast cancer," *N. Engl. J. Med.*, 347:1999-2009 (2002).
Van Der Flier et al., "Bcar1/p130Cas protein and primary breast cancer: prognosis and response to tamoxifen treatment," *J. Natl. Cancer Inst.*, 92(2):120-127 (2000).
Van Rijnsoever et al., "Characterisation of colorectal cancers showing hypermethylation at multiple CpG islands," *Gut*, 51(6):797-802 (2002).
Van Slooten et al., "Expression of Bcl-2 in node-negative breast cancer is associated with various prognostic factors, but does not predict response to one course of perioperative chemotherapy," *Br. J. Cancer*, 74(1):78-85 (1996).
Wang et al., "Gene-expression profiles to predict distant metastasis of lymph-node-negative primary breast cancer," *Lancet*, 365(9460):671-679 (2005).
West et al., "Predicting the clinical status of human breast cancer by using gene expression profiles," *Proc. Natl. Acad. Sci. USA*, 98(20):11462-11467 (2001).
Wickerham, "Tamoxifen—an update on current data and where it can now be used," *Breast Cancer Res. Treat.*, 75:S7-S12 (2002).
Wijayarante et al., "Comparative analyses of mechanistic differences among antiestrogens," *Endocrinol.*, 140(12):5828-5840 (1999).
Willson et al., "Dissection of the molecular mechanism of action of GW5638, a novel estrogen ligand, provides insights into the role of estrogen receptor in bone," *Endocrinol*, 138(9):3901-3911 (1997).
Wu, "Analysing gene expression data from DNA microarrays to identify candidate genes," *J. Pathol.*, 195:53-65 (2001).
Xiong et al., "Biomarker identification by feature wrappers," *Genome Res.*, 11:1878-1887 (2001).
Yamamoto et al., "Differential involvement of the hypermethylator phenotype in hereditary and sporadic colorectal cancers with high-frequency microsatellite instability," *Genes, Chromosomes & Cancer*, 33:322-325 (2002).
Yamamoto et al., "Overexpression of BUBR1 is associated with chromosomal instability in bladder cancer," *Cancer Genet. Cytogenet.*, 174(1):42-47 (2007).
Yang et al., "Normalization for cDNA microarray data: a robust composite method addressing single and multiple slide systematic variation," *Nucleic Acids Res.*, 30(4):e15 (2002).
Yeang et al., "Molecular classification of mulitple tumor types," *Bioinformatics*,17(Suppl. 1):S316-S322 (2001).
Yuan et al., "Increase expression of mitotic checkpoint genes in breast cancer cells with chromosomal instability," *Clin. Cancer Res.*, 12(2):405-410 (2006).
Zhou et al., "A novel transcription factor, ELF5, belongs to the ELF subfamily of ETS genes and maps to human chromosome 11p13-15, a region subject to LOH and rearrangement in human carcinoma cell lines," *Oncogene*, 17(21):2719-2732 (1998).
Zhou et al., "Overexpression of transfected human ribonucleotide reductase M2 subunit in human cancer cells enhances their invasive potential," *Clin. Exp. Metastasis*,16(1):43-49 (1998).
Zhou et al., "Tumour amplified kinase STK15/BTAK induces centrosome amplification, aneuploidy and transformation," *Nat. Genet.*,20(2):189-193 (1998).
Zuncai et al., "The prognostic biomarkers HOXB13, IL17BR, and CHDH are regulated by estrogen in breast cancer," *Clin. Cancer Res.*, 13(21):6327-6334 (2007).
Goss et al., "Late extended adjuvant treatment with letrozole improves outcome in women with early-stage breast cancer who complete 5 years of tamoxifen," J. Clin. Oncol., (2008), 1948-1955, 26(12).

\* cited by examiner

POST-TREATMENT BREAST CANCER PROGNOSIS

RELATED APPLICATIONS

This application is a continuation of U.S. application Ser. No. 13/914,617 filed Jun. 10, 2013 (now abandoned), which is a continuation of PCT Application PCT/US2011/064290, filed Dec. 9, 5 2011 and published as WO 2012/079059 with designation of the U.S., and which claims benefit of priority to U.S. Provisional Patent Application 61/421,627, filed Dec. 9, 2010, each of which is hereby incorporated by reference in its entirety as if fully set forth herein.

This application is related to International Application No. PCT/US2008/075528, filed on Sep. 6, 2008 (published as WO 2009/108215 A1) with designation of the U.S., and to U.S. patent application Ser. No. 12/718,973, filed Mar. 6, 2010. Both applications are hereby incorporated by reference as if fully set forth herein.

FIELD OF THE DISCLOSURE

The disclosure relates to the identification and use of gene expression profiles, or patterns, with clinical relevance to breast cancer. In particular, the disclosure is based in part on the identities of genes that are expressed in correlation with the likelihood of cancer recurrence after initial treatment with an aromatase inhibitor or other endocrine therapy. The levels of gene expression form a molecular index that is able to predict clinical outcome, and so prognosis, for a patient after initial treatment with an aromatase inhibitor or other endocrine therapy.

The gene expression profiles, whether embodied in nucleic acid expression, protein expression, or other expression formats, may be used to predict the post-treatment clinical outcome of subjects afflicted with breast cancer, predict cancer recurrence, and/or predict occurrence of metastatic cancer. The profiles may also be used in the study of a subject's prognosis. When used for prognosis, the profiles are used to determine the treatment of cancer based upon the likelihood of life expectancy, cancer recurrence, and/or cancer metastasis.

BACKGROUND OF THE DISCLOSURE

The treatment of breast cancer has been a field of intense interest and study. After initial diagnosis of breast cancer by analysis of a sample of breast cancer cells from a subject, treatment methods often begin with surgical removal of the tumor cells. In cases of hormone-dependent breast cancer, such as estrogen receptor positive (ER+) breast cancer, the surgery is followed by antagonizing estrogen to reduce tumor growth or re-growth. In many cases, treatment with the anti-estrogen tamoxifen is used for five years to reduce the risk of disease recurrence and so breast cancer mediated mortality.

Unfortunately, data from the field indicate that more than half of all breast cancer recurrences occur after five years of treatment with adjuvant tamoxifen.

Goss et al. (*J. Clin. Oncol.*, 26(12):1948-1955, 2008) report results from a trial examining the use of letrozole started within 3 months after five years of adjuvant tamoxifen in subjects with primary ER+ breast cancer. The results suggested that post-tamoxifen treatment with letrozole improves breast cancer-free survival and distant breast cancer-free survival.

But Goss et al. provided no means by which to predict which subjects, treated for five years with tamoxifen, would benefit from subsequent letrozole treatment. Therefore, there was no means to direct letrozole treatment only to the subjects for whom a benefit is expected. So letrozole treatment was applied to subjects for whom no benefit would have been expected, resulting in an overtreatment of the population of breast cancer-free subjects treated with for five years with tamoxifen.

The citation of documents herein is not to be construed as reflecting an admission that any is relevant prior art. Moreover, their citation is not an indication of a search for relevant disclosures. All statements regarding the dates or contents of the documents is based on available information and is not an admission as to their accuracy or correctness.

BRIEF SUMMARY OF THE DISCLOSURE

The disclosure is based in part on the discovery and determination of gene expression levels in breast cancer tumor cells that are correlated with a beneficial switch in anti-breast cancer chemotherapy. In some cases, the switch is from one form of endocrine therapy to another. The expression levels may be used to provide prognostic information, such as cancer recurrence, and predictive information, such as responsiveness to certain therapies.

In a first aspect, the disclosure includes a method to identify, or classify, a population of subjects initially treated with an anti-estrogen or anti-aromatase therapy into at least two subpopulations. A first subpopulation would be expected to benefit from a switch in therapy, such as a switch to another anti-estrogen or anti-aromatase therapy. A second subpopulation would not be expected to benefit. In some cases, the initial therapy is with tamoxifen, such as adjuvant tamoxifen therapy for a period of about five years or less. Optionally, the switch is to letrozole, or other anti-aromatase, therapy. The disclosure includes means for a population of subjects treated in this manner, and breast cancer-free during treatment, to be classified into the first, and/or the second, subpopulations.

The methods of the disclosure are based on the expression levels of certain genes, including the expression level of HoxB13, in breast cancer cells of a subject. In some embodiments, a two-gene ratio of HoxB13 expression to IL17BR expression (or HoxB13:IL17BR ratio) may be used (see Ma et al., *J. Clin. Oncol.*, 24:4611-9 (2006). In alternative embodiments, a two-gene ratio of HoxB13 expression to CHDH expression may be used.

The HoxB13:IL17BR (H:I) ratio was discovered based upon a study of novel biomarkers predictive of clinical outcome beyond standard prognostic factors. Patients who developed cancer recurrences were matched to those who did not with respect to tumor stage and grade. The simple H:I ratio was found to be suitable for predicting cancer recurrence in patients with estrogen receptor-positive (ER+) breast cancer receiving adjuvant tamoxifen therapy. Subsequent studies (Goetz et al., *Clin Cancer Res.* 12:2080-7 (2006); Jerevall et al., *Breast Cancer Res. Treat* (2007); Jansen et al., *J. Clin. Oncol.* 25:662-8 (2007)) have further shown that the ratio is both prognostic, such as by being an indicator of tumor aggressiveness, and predictive of tamoxifen benefit within both retrospective and randomized clinical trials.

In further embodiments, the disclosure includes one or more additional genes in combination with HoxB13 expression. The combination may be with any one, two, three, four or all five of the additionally disclosed genes as follows.

The additional genes of the disclosure encode Bub1B ("budding uninhibited by benzimidazoles 1 beta") or p21 protein-activated kinase 6 (PAK6); CENPA (centromere protein A, isoform a); NEK2 (NIMA-related kinase 2 or "never in mitosis gene a"-related kinase 2); RACGAP1 (Rac GTPase activating protein 1); and RRM2 (ribonucleotide reductase M2). The use of these five genes alone is referred to herein as the Molecular Grade Index (MGI). Aspects of the disclosure include compositions and methods are described for the use of HoxB13 expression, with or without IL17BR expression, in combination with expression level(s) of one or more of the above five genes to study, to provide prognostic information, and/or provide predictions of clinical responsiveness.

Thus the disclosure is based in part on the discovery that gene expression level(s) are useful for providing prognostic determinations (such as the likelihood of cancer recurrence in the form of breast cancer recurrence either locally or distally or in the form of metastasis) and predictive determinations (such as responsiveness to a course of treatment) for a subject. The use of all seven disclosed genes is referred to as the Breast Cancer Index (BCI).

When the expression levels of the BCI were analyzed using real-time reverse transcription-polymerase chain reaction (RT-PCR), the combination was found to provide superior stratification of risk of recurrence in subjects treated with five years of tamoxifen therapy. This reflects an unexpected discovery because it identifies for the first time a predictor for beneficial switching of breast cancer therapies.

In additional aspects, HoxB13 expression, and/or the BCI, may be used to predict late recurrence of cancer in a breast cancer patient. Non-limiting examples of late recurrence include after 5 years of treatment with tamoxifen, but also includes after 4 years, after 3 years, or after 2 years or less time of treatment with tamoxifen. Similarly, HoxB13 expression, and/or the BCI, may be used to predict responsiveness to letrozole or other anti-estrogen or anti-aromatase therapy after the above time periods to inhibit late recurrence.

Embodiments of the disclosure include an assay method with prognostic value and predictive value for stratifying subjects with original ER+ breast cancer and subsequent breast cancer-free treatment. As a prognostic, the stratification may be based on differential expression levels that correlate with, and so indicate, need for a switch in breast cancer therapies as a non-limiting example. As a non-limiting example, the stratification (based on expression levels) may be used to predict endocrine sensitivity (such as sensitivity to letrozole as a non-limiting example) and/or prediction of benefit from anti-estrogen and/or anti-aromatase inhibitors. The detection of gene expression may of course be in any suitable cell containing sample as described herein. Non-limiting examples of cells for use in the disclosure include those freshly isolated from the subject, those frozen after isolation, and those that are fixed and/or embedded, such as formalin fixed, paraffin embedded (FFPE). In most embodiments, the cells are breast cells, such as breast cancer cells.

In some embodiments, a method based on the expression levels is advantageously used on a breast cancer cell containing sample from a subject, such as a DCIS sample. As a non-limiting example, the cell may be one from a pre-operative histological sample used to diagnose cancer in the subject. For such a subject, the standard of care is surgery, with breast conserving surgery preferred over a radical mastectomy, to remove the DCIS. This is often followed by post-operative radiotherapy, optionally with endocrine therapy, such as treatment with tamoxifen, a selective estrogen receptor modulator (SERM), a selective estrogen receptor down-regulator (SERD), or an aromatase inhibitor (AI) such as letrozole. In other post-operative cases, endocrine therapy is administered without radiation, and optionally with chemotherapy.

The instant disclosure is directed to the identification of a subject as expected to benefit from a switch in endocrine therapy, such as from one type of endocrine therapy to another, after breast cancer-free survival during the course of the initial endocrine therapy. In additional embodiments, the switch may be made after an initial course of endocrine therapy for 5 years, 4 years, 3 years, or 2 years.

The disclosure also includes detecting gene expression where high HoxB13 expression is an indicator of increased likelihood of cancer recurrence in the subject following an initial endocrine therapy, such as adjuvant tamoxifen therapy. The methods may thus include identifying the subject as likely, or unlikely, to experience local cancer recurrence, and further include switching treatment modalities for the subject to address the expected outcome. As a non-limiting example, determination of a likelihood of recurrence in the absence of an extended, post-initial treatment, therapy may be used to confirm the suitability of, or to select, an extended therapy with a switch in the anti-estrogen and/or anti-aromatase modality used.

In some cases, the disclosed methods may be used to select or eliminate therapies for premenopausal women, or for postmenopausal women, that have undergone treatment with endocrine therapy and remained cancer-free during that time. Premenopausal women include those who are less than about 35 years of age. The method may include assaying a breast cancer cell containing sample from a subject for expression of the disclosed genes. As a non-limiting example, the cell may be one from a pre-operative histological sample used to diagnose cancer in the subject.

Non-limiting examples of endocrine therapy include treatment with an SERM, such as tamoxifen, or an SERD, or an aromatase inhibitor (AI). Non-limiting examples of an AI include non-steroidal inhibitors such as letrozole and anastrozole and irreversible steroidal inhibitors such as exemestane.

DETAILED DESCRIPTION OF MODES OF PRACTICING THE DISCLOSURE

Definitions of Terms as Used Herein

A gene expression "pattern" or "profile" or "signature" refers to the relative expression of one or more genes between two or more clinical outcomes, cancer outcomes, cancer recurrence and/or survival outcomes which is correlated with being able to distinguish between said outcomes. In some cases, the outcome is that of breast cancer.

A "gene" is a polynucleotide that encodes a discrete product, whether RNA or proteinaceous in nature. It is appreciated that more than one polynucleotide may be capable of encoding a discrete product. The term includes alleles and polymorphisms of a gene that encodes the same product, or a functionally associated (including gain, loss, or modulation of function) analog thereof, based upon chromosomal location and ability to recombine during normal mitosis.

The terms "correlate" or "correlation" or equivalents thereof refer to an association between expression of one or more genes and a physiologic state of a cell to the exclusion of one or more other state as identified by use of the methods as described herein. A gene may be expressed at a higher or a lower level and still be correlated with one or more cancer state or outcome.

A "polynucleotide" is a polymeric form of nucleotides of any length, either ribonucleotides or deoxyribonucleotides. This term refers only to the primary structure of the molecule. Thus, this term includes double- and single-stranded DNA and RNA. It also includes known types of modifications including labels known in the art, methylation, "caps", substitution of one or more of the naturally occurring nucleotides with an analog, and internucleotide modifications such as uncharged linkages (e.g., phosphorothioates, phosphorodithioates, etc.), as well as unmodified forms of the polynucleotide.

The term "amplify" is used in the broad sense to mean creating an amplification product can be made enzymatically with DNA or RNA polymerases. "Amplification," as used herein, generally refers to the process of producing multiple copies of a desired sequence, particularly those of a sample. "Multiple copies" mean at least 2 copies. A "copy" does not necessarily mean perfect sequence complementarity or identity to the template sequence.

By corresponding is meant that a nucleic acid molecule shares a substantial amount of sequence identity with another nucleic acid molecule. Substantial amount means at least 95%, usually at least 98% and more usually at least 99%, and sequence identity is determined using the BLAST algorithm, as described in Altschul et al., *J. Mol. Biol.* 215:403-410 (1990) (using the published default setting, i.e. parameters w=4, t=17). Methods for amplifying mRNA are generally known in the art, and include reverse transcription PCR (RT-PCR) and those described in U.S. patent application Ser. No. 10/062,857 (filed on Oct. 25, 2001), as well as U.S. Provisional Patent Applications 60/298,847 (filed Jun. 15, 2001) and 60/257,801 (filed Dec. 22, 2000), all of which are hereby incorporated by reference in their entireties as if fully set forth. Another method which may be used is quantitative PCR (or Q-PCR). Alternatively, RNA may be directly labeled as the corresponding cDNA by methods known in the art.

A "microarray" is a linear or two-dimensional array of preferably discrete regions, each having a defined area, formed on the surface of a solid support such as, but not limited to, glass, plastic, or synthetic membrane. The density of the discrete regions on a microarray is determined by the total numbers of immobilized polynucleotides to be detected on the surface of a single solid phase support, preferably at least about 50/cm$^2$, more preferably at least about 100/cm$^2$, even more preferably at least about 500/cm$^2$, but preferably below about 1,000/cm$^2$. Preferably, the arrays contain less than about 500, about 1000, about 1500, about 2000, about 2500, or about 3000 immobilized polynucleotides in total. As used herein, a DNA microarray is an array of oligonucleotides or polynucleotides placed on a chip or other surfaces used to hybridize to amplified or cloned polynucleotides from a sample. Since the position of each particular group of primers in the array is known, the identities of a sample polynucleotides can be determined based on their binding to a particular position in the microarray.

Because the disclosure relies upon the identification of genes that are over- or under-expressed, one embodiment of the disclosure involves determining expression by hybridization of mRNA, or an amplified or cloned version thereof, of a sample cell to a polynucleotide that is unique to a particular gene sequence. Preferred polynucleotides of this type contain at least about 20, at least about 22, at least about 24, at least about 26, at least about 28, at least about 30, or at least about 32 consecutive basepairs of a gene sequence that is not found in other gene sequences. The term "about" as used in the previous sentence refers to an increase or decrease of 1 from the stated numerical value. Even more preferred are polynucleotides of at least or about 50, at least or about 100, at least about or 150, at least or about 200, at least or about 250, at least or about 300, at least or about 350, or at least or about 400 basepairs of a gene sequence that is not found in other gene sequences. The term "about" as used in the preceding sentence refers to an increase or decrease of 10% from the stated numerical value. Such polynucleotides may also be referred to as polynucleotide probes that are capable of hybridizing to sequences of the genes, or unique portions thereof, described herein. Preferably, the sequences are those of mRNA encoded by the genes, the corresponding cDNA to such mRNAs, and/or amplified versions of such sequences. In preferred embodiments of the disclosure, the polynucleotide probes are immobilized on an array, other devices, or in individual spots that localize the probes.

In another embodiment of the disclosure, all or part of a disclosed sequence may be amplified and detected by methods such as the polymerase chain reaction (PCR) and variations thereof, such as, but not limited to, quantitative PCR (Q-PCR), reverse transcription PCR (RT-PCR), and real-time PCR, optionally real-time RT-PCR. Such methods would utilize one or two primers that are complementary to portions of a disclosed sequence, where the primers are used to prime nucleic acid synthesis. The newly synthesized nucleic acids are optionally labeled and may be detected directly or by hybridization to a polynucleotide of the disclosure. The newly synthesized nucleic acids may be contacted with polynucleotides (containing sequences) of the disclosure under conditions which allow for their hybridization.

Alternatively, and in another embodiment of the disclosure, gene expression may be determined by analysis of expressed protein in a cell sample of interest by use of one or more antibodies specific for one or more epitopes of individual gene products (proteins) in said cell sample. Such antibodies are preferably labeled to permit their easy detection after binding to the gene product.

The term "label" refers to a composition capable of producing a detectable signal indicative of the presence of the labeled molecule. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "support" refers to conventional supports such as beads, particles, dipsticks, fibers, filters, membranes and silane or silicate supports such as glass slides.

As used herein, a "cancer tissue sample" or "cancer cell sample" refers to a cell containing sample of tissue isolated from an individual afflicted with the corresponding cancer. The sample may be from material removed via a surgical procedure, such as a biopsy. Such samples are primary isolates (in contrast to cultured cells) and may be collected by any suitable means recognized in the art. In some embodiments, the "sample" may be collected by an non-invasive method, including, but not limited to, abrasion, fine needle aspiration.

A "breast tissue sample" or "breast cell sample" refers to a sample of breast tissue or fluid isolated from an individual suspected of being afflicted with, or at risk of developing, breast cancer. Such samples are primary isolates (in contrast to cultured cells) and may be collected by any non-invasive means, including, but not limited to, ductal lavage, fine needle aspiration, needle biopsy, the devices and methods described in U.S. Pat. No. 6,328,709, or any other suitable means recognized in the art. Alternatively, the "sample" may be collected by an invasive method, including, but not limited to, surgical biopsy.

"Expression" and "gene expression" include transcription and/or translation of nucleic acid material. Of course the term may also be limited, if so indicated, as referring only to the transcription of nucleic acids.

As used herein, the term "comprising" and its cognates are used in their inclusive sense; that is, equivalent to the term "including" and its corresponding cognates.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in the sequence of a gene disclosed herein interest in comparison to a reference sequence. A sequence mutation includes single nucleotide changes, or alterations of more than one nucleotide in a sequence, due to mechanisms such as substitution, deletion or insertion. Single nucleotide polymorphism (SNP) is also a sequence mutation as used herein. Because the present disclosure is based on the relative level of gene expression, mutations in non-coding regions of genes as disclosed herein may also be assayed in the practice of the disclosure.

"Detection" includes any means of detecting, including direct and indirect detection of gene expression and changes therein. For example, "detectably less" products may be observed directly or indirectly, and the term indicates any reduction (including the absence of detectable signal). Similarly, "detectably more" product means any increase, whether observed directly or indirectly.

Increases and decreases in expression of the disclosed sequences are defined in the following terms based upon percent or fold changes over expression in normal cells. Increases may be of 10, 20, 30, 40, 50, 60, 70, 80, 90, 100, 120, 140, 160, 180, or 200% relative to expression levels in normal cells. Alternatively, fold increases may be of 1, 1.5, 2, 2.5, 3, 3.5, 4, 4.5, 5, 5.5, 6, 6.5, 7, 7.5, 8, 8.5, 9, 9.5, or 10 fold over expression levels in normal cells. Decreases may be of 10, 20, 30, 40, 50, 55, 60, 65, 70, 75, 80, 82, 84, 86, 88, 90, 92, 94, 96, 98, 99 or 100% relative to expression levels in normal cells.

Unless defined otherwise all technical and scientific terms used herein have the same meaning as commonly understood to one of ordinary skill in the art to which this disclosure belongs.

General

The gene expression patterns disclosed herein are predictive factors for therapeutic benefit in a switch in endocrine therapy. In some cases, the prediction is in node-negative breast cancer patients, such as ER+ node-negative patients as a non-limiting example.

To determine the expression levels of genes in the practice of the present disclosure, any method known in the art may be utilized. In some embodiments, expression based on detection of RNA which hybridizes to the genes identified and disclosed herein is used. This is readily performed by any RNA detection or amplification+detection method known or recognized as equivalent in the art such as, but not limited to, reverse transcription-PCR, the methods disclosed in U.S. patent application Ser. No. 10/062,857 (filed on Oct. 25, 2001) as well as U.S. Provisional Patent Application 60/298,847 (filed Jun. 15, 2001) and 60/257,801 (filed Dec. 22, 2000), and methods to detect the presence, or absence, of RNA stabilizing or destabilizing sequences.

Alternatively, expression based on detection of DNA status may be used. Detection of the DNA of an identified gene as methylated or deleted may be used for genes that have decreased expression. This may be readily performed by PCR based methods known in the art, including, but not limited to, Q-PCR. Conversely, detection of the DNA of an identified gene as amplified may be used for genes that have increased expression in correlation with a particular breast cancer outcome. This may be readily performed by PCR based, fluorescent in situ hybridization (FISH) and chromosome in situ hybridization (CISH) methods known in the art.

Expression based on detection of a presence, increase, or decrease in protein levels or activity may also be used. Detection may be performed by any immunohistochemistry (IHC) based, blood based (especially for secreted proteins), antibody (including autoantibodies against the protein) based, exfoliate cell (from the cancer) based, mass spectroscopy based, and image (including used of labeled ligand) based method known in the art and recognized as appropriate for the detection of the protein. Antibody and image based methods are additionally useful for the localization of tumors after determination of cancer by use of cells obtained by a non-invasive procedure (such as ductal lavage or fine needle aspiration), where the source of the cancerous cells is not known. A labeled antibody or ligand may be used to localize the carcinoma(s) within a patient.

One embodiment using a nucleic acid based assay to determine expression is by immobilization of one or more sequences of the genes identified herein on a solid support, including, but not limited to, a solid substrate as an array or to beads or bead based technology as known in the art. Alternatively, solution based expression assays known in the art may also be used.

The immobilized gene(s) may be in the form of polynucleotides that are unique or otherwise specific to the gene(s) such that the polynucleotide would be capable of hybridizing to a DNA or RNA corresponding to the gene(s). These polynucleotides may be the full length of the gene(s) or be short sequences of the genes (up to one nucleotide shorter than the full length sequence known in the art by deletion from the 5' or 3' end of the sequence) that are optionally minimally interrupted (such as by mismatches or inserted non-complementary basepairs) such that hybridization with a DNA or RNA corresponding to the gene(s) is not affected. In some cases, the polynucleotides used are from the 3' end of the gene, such as within about 350, about 300, about 250, about 200, about 150, about 100, or about 50 nucleotides from the polyadenylation signal or polyadenylation site of a gene or expressed sequence. Polynucleotides containing mutations relative to the sequences of the disclosed genes may also be used so long as the presence of the mutations still allows hybridization to produce a detectable signal.

The immobilized gene(s) may be used to determine the state of nucleic acid samples prepared from sample cancer, or breast, cell(s) for which the outcome of the sample's subject (e.g. patient from whom the sample is obtained) is not known or for confirmation of an outcome that is already assigned to the sample's subject. Without limiting the disclosure, such a cell may be from a patient with ER+ breast cancer. The immobilized polynucleotide(s) need only be sufficient to specifically hybridize to the corresponding nucleic acid molecules derived from the sample under suitable conditions.

As will be appreciated by those skilled in the art, some of the corresponding sequences noted above include 3' poly A (or poly T on the complementary strand) stretches that do not contribute to the uniqueness of the disclosed sequences. The disclosure may thus be practiced with sequences lacking the 3' poly A (or poly T) stretches. The uniqueness of the disclosed sequences refers to the portions or entireties of the sequences which are found only in the disclosed gene's nucleic acids, including unique sequences found at the 3' untranslated portion of the genes. Preferred unique sequences for the practice of the disclosure are those which contribute to the consensus sequences for each of the three sets such that the unique sequences will be useful in detecting expression in a variety of individuals rather than being specific for a polymorphism present in some individuals. Alternatively, sequences unique to an individual or a subpopulation may be used. The preferred unique sequences are preferably of the lengths of polynucleotides of the disclosure as discussed herein.

To determine the (increased or decreased) expression levels of the above described sequences in the practice of the disclosure, any method known in the art may be utilized. In one embodiment of the disclosure, expression based on detection of RNA which hybridizes to polynucleotides containing the above described sequences is used. This is readily performed by any RNA detection or amplification+ detection method known or recognized as equivalent in the art such as, but not limited to, reverse transcription-PCR (optionally real-time PCR), the methods disclosed in U.S. patent application Ser. No. 10/062,857 entitled "Nucleic Acid Amplification" filed on Oct. 25, 2001 as well as U.S. Provisional Patent Application 60/298,847 (filed Jun. 15, 2001) and 60/257,801 (filed Dec. 22, 2000), the methods disclosed in U.S. Pat. No. 6,291,170, and quantitative PCR. Methods to identify increased RNA stability (resulting in an observation of increased expression) or decreased RNA stability (resulting in an observation of decreased expression) may also be used. These methods include the detection of sequences that increase or decrease the stability of mRNAs containing the genes' sequences. These methods also include the detection of increased mRNA degradation.

In some embodiments of the disclosure, polynucleotides having sequences present in the 3' untranslated and/or non-coding regions of the above disclosed sequences are used to detect expression levels of the gene sequences in cancer, or breast, cells. Such polynucleotides may optionally contain sequences found in the 3' portions of the coding regions of the above disclosed sequences. Polynucleotides containing a combination of sequences from the coding and 3' non-coding regions preferably have the sequences arranged contiguously, with no intervening heterologous sequences.

Alternatively, the disclosure may be practiced with polynucleotides having sequences present in the 5' untranslated and/or non-coding regions of the gene sequences in cancer, or breast, cells to detect their levels of expression. Such polynucleotides may optionally contain sequences found in the 5' portions of the coding regions. Polynucleotides containing a combination of sequences from the coding and 5' non-coding regions preferably have the sequences arranged contiguously, with no intervening heterologous sequences.

The disclosure may also be practiced with sequences present in the coding regions of the disclosed gene sequences.

Non-limiting polynucleotides contain sequences from 3' or 5' untranslated and/or non-coding regions of at least about 20, at least about 22, at least about 24, at least about 26, at least about 28, at least about 30, at least about 32, at least about 34, at least about 36, at least about 38, at least about 40, at least about 42, at least about 44, or at least about 46 consecutive nucleotides. The term "about" as used in the previous sentence refers to an increase or decrease of 1 from the stated numerical value. Even more preferred are polynucleotides containing sequences of at least or about 50, at least or about 100, at least about or 150, at least or about 200, at least or about 250, at least or about 300, at least or about 350, or at least or about 400 consecutive nucleotides. The term "about" as used in the preceding sentence refers to an increase or decrease of 10% from the stated numerical value.

Sequences from the 3' or 5' end of the above described coding regions as found in polynucleotides of the disclosure are of the same lengths as those described above, except that they would naturally be limited by the length of the coding region. The 3' end of a coding region may include sequences up to the 3' half of the coding region. Conversely, the 5' end of a coding region may include sequences up the 5' half of the coding region. Of course the above described sequences, or the coding regions and polynucleotides containing portions thereof, may be used in their entireties.

Polynucleotides combining the sequences from a 3' untranslated and/or non-coding region and the associated 3' end of the coding region may be at least or about 100, at least about or 150, at least or about 200, at least or about 250, at least or about 300, at least or about 350, or at least or about 400 consecutive nucleotides. Preferably, the polynucleotides used are from the 3' end of the gene, such as within about 350, about 300, about 250, about 200, about 150, about 100, or about 50 nucleotides from the polyadenylation signal or polyadenylation site of a gene or expressed sequence. Polynucleotides containing mutations relative to the sequences of the disclosed genes may also be used so long as the presence of the mutations still allows hybridization to produce a detectable signal.

In another embodiment of the disclosure, polynucleotides containing deletions of nucleotides from the 5' and/or 3' end of the above disclosed sequences may be used. The deletions are preferably of 1-5, 5-10, 10-15, 15-20, 20-25, 25-30, 30-35, 35-40, 40-45, 45-50, 50-60, 60-70, 70-80, 80-90, 90-100, 100-125, 125-150, 150-175, or 175-200 nucleotides from the 5' and/or 3' end, although the extent of the deletions would naturally be limited by the length of the disclosed sequences and the need to be able to use the polynucleotides for the detection of expression levels.

Other polynucleotides of the disclosure from the 3' end of the above disclosed sequences include those of primers and optional probes for quantitative PCR. In some embodiments, the primers and probes are those which amplify a region less than about 350, less than about 300, less than about 250, less than about 200, less than about 150, less than about 100, or less than about 50 nucleotides from the from the polyadenylation signal or polyadenylation site of a gene or expressed sequence.

In yet other embodiments of the disclosure, polynucleotides containing portions of the above disclosed sequences including the 3' end may be used. Such polynucleotides would contain at least or about 50, at least or about 100, at least about or 150, at least or about 200, at least or about 250, at least or about 300, at least or about 350, or at least or about 400 consecutive nucleotides from the 3' end of the disclosed sequences.

The disclosure also includes polynucleotides used to detect gene expression in breast cells. The polynucleotides may comprise a shorter polynucleotide consisting of sequences found in the above genes in combination with heterologous sequences not naturally found in combination with the sequences. Non-limiting examples include short sequences from cloning vectors or present in restriction fragments used to prepare labeled probes or primers as described herein.

HoxB13 and H/I

The methods of the disclosure based on the expression levels of HoxB13 in breast cancer cells of a subject may be used as a predictor of benefit in switching endocrine therapy after an initial course of endocrine therapy. In some embodiments, a two-gene ratio of HoxB13 expression to IL17BR expression (or HoxB13:IL17BR ratio) may be used in the manner reported by Ma et al. (*J. Clin. Oncol.*, 24:4611-9 (2006). In alternative embodiments, a two-gene ratio of HoxB13 expression to CHDH expression may be used.

In cases using HoxB13 expression alone or the HoxB13:IL17BR (H:I) ratio, a cutoff value may be used to define breast cancer cells as having either a "high" and a "low" value corresponding to the expression. In some embodiments, a cutoff may be used to define breast cancer cells as having either a "high H/I" and a "low H/I" value. As a non-limiting example, the value of 0.06 may be used in the manner of Ma et al. In other embodiments, the cutoff may be the average expression of HoxB13 in breast cancer cells from afflicted subjects. In additional possible embodiments, the cutoff may be the average value of H/I in breast cancer cells from afflicted subjects as determined by the average HoxB13 expression/the average IL17BR expression.

MGI

The genes disclosed below have roles in the cell cycle and reported peak expression as follows:

| Gene | Peak of Expression | Role in Cell Cycle |
| --- | --- | --- |
| BUB1B | G2/M | mitotic spindle assembly checkpoint |
| CENPA | G2/M | centromere assembly |
| NEK2 | G2/M | centrosome duplication |
| RACGAP1 | Not Determined | Initiation of cytokinesis |
| RRM2 | S | DNA replication |

The sequences of these genes have been previously reported and characterized in the field. For example, and on Sep. 6, 2007, the human BUB1B (also known as p21 protein-activated kinase 6 or PAK6) gene was identified by Unigene Hs.631699 and was characterized by 273 corresponding sequences. On Mar. 6, 2010, the same gene information was identified by UniGene Hs.513645 and characterized as corresponding to chromosome 15 at position 15q14 and as supported by 23 mRNA sequences and 549 EST sequences.

Also on Sep. 6, 2007, the human CENPA gene was identified by Hs.1594 (with 129 corresponding sequences). On Mar. 6, 2010, the same gene information was characterized as corresponding to chromosome 2 at 2p24-p21 and as supported by 10 mRNA sequences and 119 EST sequences.

Also on Sep. 6, 2007, the human NEK2 gene was identified by Hs.153704 (with 221 corresponding sequences). On Mar. 6, 2010, the same gene information was characterized as corresponding to chromosome 1 at 1q32.2-q41 and as supported by 17 mRNA sequences and 205 EST sequences.

Also on Sep. 6, 2007, the human RACGAP1 gene was identified by Hs.696319 (with 349 corresponding sequences). On Mar. 6, 2010, the same gene information was identified by UniGene Hs.505469 and characterized as corresponding to chromosome 12 at position 12q13.12 and as supported by 15 mRNA sequences and 398 EST sequences.

Also on Sep. 6, 2007, the human RRM2 gene was identified by Hs.226390 (with 1348 corresponding sequences). On Mar. 6, 2010, the same gene information was characterized as corresponding to chromosome 2 at 2p25-p24 and as supported by 25 mRNA sequences and 1328 EST sequences.

The mRNA and EST sequences corresponding to each of the above Unigene identifiers are hereby incorporated by reference as if fully set forth and may be used in the practice of the disclosure by the skilled person as deemed appropriate. Representative mRNA sequences for each of BUB1B, CENPA, NEK2, RACGAP1, and RRM2 have been disclosed in U.S. patent application Ser. No. 12/718,973, published as US 2011-0136680 A1 on Jun. 9, 2011. The disclosed sequences are non-limiting for the practice of the disclosed invention and are provided as evidence of the substantial knowledge in the field regarding sequences that are the disclosed genes. Additionally, the skilled person is fully capable of aligning any two or more of the known expressed sequences for each of these genes to identify an area of identity or conserved changes as a region that uniquely identifies each of these genes in comparison to other genes. Furthermore, the skilled person is fully capable of aligning any two or more of the known expressed sequences for each of these genes to identify an area unique to one or more of the of the expressed sequences as a region that uniquely identifies one known expressed sequence relative to at least one other expressed sequence. As a non-limiting example, a unique region may be in a variant of the expressed sequence for one of the known genes such that the region may be used to identify expression of the variant.

The sequences of the same genes have also been identified and characterized from other animal species. Thus the skilled person in the field is clearly aware of how to identify the disclosed genes relative to other animal genes. The skilled person may also optionally compare the known sequences of the disclosed genes from different animal sources to identify conserved regions and sequences unique to these genes relative to other genes.

Methods

As described herein, the disclosure includes the identity of genes, the expression of which can be used to provide prognostic information related to cancer. In particular, the expression levels of these genes may be used in relation to breast cancer. In some methods, the gene expression profile correlates with (and so are able to discriminate between) patients expected to benefit from a switch in endocrine therapy following an initial treatment with endocrine therapy for a period of time. In other embodiments, the disclosure includes a method to compare gene expression in a sample of cancer cells from a patient to the gene expression profile to determine the likely clinical or treatment outcome for the patient, or natural biological result, in the absence of a switch.

These embodiments of the disclosure may be advantageously used to meet an important unmet diagnostic need for the ability to predict whether a patient will likely benefit from a switch in treatment type. For example, a high H:I ratio value is strongly associated with response to a switch from first-line tamoxifen therapy for up to 5 years to letrozole therapy. The switch may occur anytime following the first-line therapy, such as immediately afterward, within three months after termination of first-line therapy, within six months after termination of first-line therapy, within nine months after termination of first-line therapy, within 12 months after termination of first-line therapy, within 18 months after termination of first-line therapy, or within 24 months (or more) after termination of first-line therapy.

So the disclosure includes a method to identify a patient, from a population of patients with ER+ breast cancer cells treated with a first endocrine therapy and cancer-free for a period of time, as belonging to a subpopulation of patients with a better prognosis if treated with an alternative endocrine therapy. In some cases, the breast cancer in the subject is node negative. The disclosure provides a non-subjective means for the identification of patients in the subpopulation.

The disclosure also includes a method of determining prognosis and/or survival outcome by assaying for the expression patterns disclosed herein. So where subjective interpretation may have been previously used to determine the prognosis and/or treatment of cancer patients, this disclosure provides objective gene expression patterns, which may used alone or in combination with subjective criteria to provide a more accurate assessment of patient outcomes, including survival and the recurrence of cancer.

In some embodiments, the disclosure provides a method to determine therapeutic treatment for a cancer patient by determining prognosis for said patient by assaying a sample of cancer cells from said patient for the expression levels described herein, and selecting a treatment for a patient with such gene expression. The assaying may include measuring or detecting or determining the expression level of the genes in any suitable means described herein or known to the skilled person. In many cases, the cancer is breast cancer, and the subject is a human patient. Additionally, the cancer cells may be those of a tumor and/or from a node negative (lymph nodes negative for cancer) or node positive (lymph nodes positive for cancer) subject.

The requisite level of expression may be that which is identified by the methods described herein for the genes used. Additionally, the assaying may include preparing RNA from the sample, optionally for use in PCR (polymerase chain reaction) or other analytical methodology as described herein. The PCR methodology is optionally RT-PCR (reverse transcription-PCR) or quantitative PCR, such as real-time RT-PCR. Alternatively, the assaying may be conducted by use of an array, such as a microarray as known in the relevant field. Optionally, the sample of cancer cells is dissected from tissue removed or obtained from said subject. As described herein, a variety of sample types may be used, including a formalin fixed paraffin embedded (FFPE) sample as a non-limiting example. And as described herein, the method may include assaying or determining the H:I ratio (ratio of HoxB13 and IL17BR expression levels) in the sample as disclosed herein.

By way of non-limiting example, all five genes of the MGI may be assayed and used to detect expression levels that correspond to a value that is "high risk" (which is above the cutoff) for MGI, or to detect expression levels that correspond to a value that is "low risk" (which is at or below the cutoff) for MGI, as disclosed herein. In some cases, the MGI cutoff threshold may be 0 (zero), such as where the measurements of expression levels are standardized to 0 (zero) with a standard deviation of 1. In alternative embodiments, the cutoff may be at or about 0.05, at or about 0.10, at or about 0.15, at or about 0.20, at or about 0.25, at or about −0.05, at or about −0.10, at or about −0.15, at or about −0.20, at or about −0.25, at or about −0.30, at or about −0.35, at or about −0.40, at or about −0.45, at or about −0.50, at or about −0.55, at or about −0.60, at or about −0.65, at or about −0.70, at or about −0.75, at or about −0.80, at or about −0.85, at or about −0.90, at or about −0.95, at or about −1.0, at or about −1.1, at or about −1.2, at or about −1.3, at or about −1.4, at or about −1.5, at or about −1.6, at or about −1.7, at or about −1.8, at or about −1.9, at or about −2.0 or lower. With respect to the H:I ratio, its determination may be made as described in Ma et al., *Cancer Cell*, 5:607-16 (2004) and Ma et al. (2006) as referenced herein. For example, a value of 0.06 may be used to determine whether a sample has a "high risk" (>0.06) or "low risk" (≤0.06) H:I ratio.

So using a threshold, or cutoff, of 0 (zero) as a non-limiting example for MGI with all five genes, the disclosed methods provide two possible assay outcomes for a given sample: "high risk MGI" corresponding to a value above 0 (zero) and "low risk MGI" corresponding to a value ≤0. A "high risk MGI" is indicative of a "high risk" cancer, including breast cancer that is analogous to that of a Grade III tumor as defined by methodologies and standards known in the field. A "low risk MGI" is indicative of a "low risk" cancer, including breast cancer, that is analogous to that of a Grade I tumor as defined by methodologies and standards known in the field.

In one embodiment of the disclosure, a method is provided for determining the risk or likelihood of cancer recurrence in a subject after treatment for breast cancer, such as removal of the cancer by surgery. The method may comprise i) preparing cDNA from nucleic acids in a sample of ER+ breast cancer cells removed from a breast cancer afflicted subject; ii) determining the expression levels of the seven genes in the disclosed Breast Cancer Index (BCI) from said cDNA to determine a BCI value; iii) identifying the subject as having been treated with endocrine therapy for a period of time without cancer recurrence; and iv) classifying the cancer as likely to recur due to a high risk BCI value. In some cases, the subject has been treated with endocrine therapy for about 5 years or more, about 4 years or more, about 3 years or more, about 2 years or more, or about 1 year or more.

In another embodiment of the disclosure, a method is provided for determining the likelihood of a beneficial switch in endocrine therapy as treatment for breast cancer. The method may comprise i) preparing cDNA from nucleic acids in a sample of ER+ breast cancer cells removed from a breast cancer afflicted subject; ii) determining the expression level of the HoxB13 gene from said cDNA; iii) optionally identifying the subject as having undergone surgical removal of the breast cancer; iv) identifying the subject as having been treated with a first endocrine therapy for a period of time without cancer recurrence; and v) classifying the subject as expected to benefit from treatment with a different second endocrine therapy after cessation of the first endocrine therapy, wherein said classifying is based upon an elevated expression level of HoxB13. In some cases, the elevated expression level of HoxB13 is determined as part of the H/I value and the classifying is based upon a high H/I value. In some cases, the subject has been treated with endocrine therapy for about 5 years or more, about 4 years or more, about 3 years or more, about 2 years or more, or about 1 year or more.

In additional embodiments, the disclosure provides a method to treat a patient that has undergone a first endocrine therapy as described above. The method may comprise the above determining the likelihood of a beneficial switch in endocrine therapy as treatment for breast cancer followed by treating the patient with a second endocrine therapy after ending treatment with the first endocrine therapy.

As non-limiting examples, the first endocrine therapy may be treatment with an SERM or an SERD and the second endocrine therapy may be treatment with an aromatase inhibitor. Alternatively, the first endocrine therapy may be treatment with an aromatase inhibitor and the second endocrine therapy may be treatment with an SERM or an SERD. Embodiments include tamoxifen as the first endocrine therapy followed by letrozole as the second, or letrozole as the first endocrine therapy followed by taxmoxifen as the second.

The disclosure further includes a method of determining a prognostic factor or predictor of clinical responsiveness in pre-menopausal women and post-menopausal women. Post-menopausal women may be defined as those that are ≥50 years old while pre-menopausal women may be defined as those who are less than 50 years old.

The ability to discriminate is conferred by the identification of expression of the individual genes as relevant and not by the form of the assay used to determine the actual level of expression. An assay may utilize any identifying feature of an identified individual gene as disclosed herein as long as the assay reflects, quantitatively or qualitatively, expression of the gene in the "transcriptome" (the transcribed fraction of genes in a genome) or the "proteome" (the translated fraction of expressed genes in a genome). Identifying features include, but are not limited to, unique nucleic acid sequences used to encode (DNA), or express (RNA), said gene or epitopes specific to, or activities of, a protein encoded by said gene. All that is required is the identity of the gene(s) necessary to discriminate between cancer outcomes and an appropriate cell containing sample for use in an expression assay.

Similarly, the nature of the cell containing sample is not limiting, as fresh tissue, freshly frozen tissue, and fixed tissue, such as formalin-fixed paraffin-embedded (FFPE) tissues, may be used in the disclosed methods.

In one embodiment, the disclosure provides for the identification of the gene expression patterns by analyzing global, or near global, gene expression from single cells or homogenous cell populations which have been dissected away from, or otherwise isolated or purified from, contaminating cells beyond that possible by a simple biopsy. Because the expression of numerous genes fluctuate between cells from different patients as well as between cells from the same patient sample, the levels of gene expression may be determined in correspondence to one or more "control" or "normalization" genes, the expression(s) of which are relatively constant in the cells of a patient or between patients.

In another aspect, the disclosure includes physical and methodological means for detecting the expression of gene(s) identified by the models generated by individual expression patterns. These means may be directed to assaying one or more aspect of the DNA template(s) underlying the expression of the gene(s), of the RNA used as an intermediate to express the gene(s), or of the proteinaceous product expressed by the gene(s).

One advantage provided by the disclosure is that contaminating, non-cancer cells (such as infiltrating lymphocytes or other immune system cells) are not present to possibly affect the genes identified or the subsequent analysis of gene expression to identify the cancer recurrence and/or survival outcomes of patients. Such contamination is present where a biopsy containing many cell types is used to assay gene expression profiles.

While the present disclosure is described mainly in the context of human cancer, such as breast cancer, it may be practiced in the context of cancer of any animal. Preferred animals for the application of the present disclosure are mammals, particularly those important to agricultural applications (such as, but not limited to, cattle, sheep, horses, and other "farm animals"), animal models of cancer, and animals for human companionship (such as, but not limited to, dogs and cats).

The methods provided by the disclosure may also be automated in whole or in part.

Kits

The materials for use in the methods of the present disclosure are ideally suited for preparation of kits produced in accordance with well known procedures. The disclosure thus provides kits comprising agents for the detection of expression of the disclosed genes for grading tumors or determining cancer outcomes. Such kits optionally comprise the agent with an identifying description or label or instructions relating to their use in the methods of the present disclosure. Such a kit may comprise containers, each with one or more of the various reagents (typically in concentrated form) utilized in the methods, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more primer complexes of the present disclosure (e.g., appropriate length poly(T) or random primers linked to a promoter reactive with the RNA polymerase). A set of instructions will also typically be included.

Having now generally provided the disclosure, the same will be more readily understood through reference to the following examples which are provided by way of illustration, and are not intended to be limiting of the disclosure, unless specified.

EXAMPLES

Example I: General

Patients and Tumor Samples

Samples from the NCIC CTG MA.17 cohort (see Goss et al., *J. Clin. Oncol.,* 26(12):1948-1955, 2008) were used. 100 cases with 200 controls were used. The 100 cases included 61 cases of distant cancer recurrence; 17 cases of local cancer recurrence; 5 cases of regional cancer recurrence; 16 cases of contralateral recurrences; and 1 unknown case. Of these, the contralateral and unknown cases were excluded.

Clinical follow-up data were available for the samples used, which were formalin-fixed paraffin-embedded (FFPE) tumor blocks from the time of diagnosis. Odds ratios were calculated with analysis of BCI, H:I, HoxB13 and MGI as continuous and categorical variables. Multivariate analysis also included age, tumor grade and treatment in the analysis. Treatment interaction: age and tumor grade were also included in the analysis. P-values were calculated for the interaction term.

Table 1 summarizes characteristics for the cases and controls (N=249).

TABLE 1

| Factor Description | | MA-17 overall (n = 5157) | Case-control study (n = 249) | Cases (n = 83) | Controls (n = 166) | P-value |
|---|---|---|---|---|---|---|
| Age | <50 | | 9 (4%) | 4 (5%) | 5 (3%) | 0.64 |
| — | >=50, <60 | | 83 (33%) | 27 (32%) | 56 (34%) | |
| | >=60, <70 | | 82 (33%) | 24 (29%) | 58 (35%) | |
| | >=70 | | 75 (30%) | 28 (34%) | 47 (28%) | |
| Tumor Grade | 1 | | 26 (10%) | 6 (7%) | 20 (12%) | 0.28 |
| | 2 | | 166 (67%) | 54 (65%) | 112 (67.5%) | |
| | 3 | | 57 (23%) | 23 (27%) | 34 (20.5%) | |
| Tumor Type | Ductal | | 218 (88%) | 71 (86%) | 147 (88.6%) | 0.63 |
| — | Lobular | | 31 (12%) | 12 (14%) | 19 (11.4%) | |
| N Stage | N0 | | 94 (38%) | 31 (37%) | 63 (38%) | 0.45 |
| | N1 | | 138 (55%) | 44 (53%) | 94 (57%) | |
| | N2, N3, NX | | 17 (7%) | 8 (10%) | 9 (5%) | |
| T Stage | T1 | | 110 (44%) | 37 (45%) | 73 (44%) | 0.58 |
| | T2 | | 111 (45%) | 35 (42%) | 76 (46%) | |
| | T3 | | 21 (8%) | 7 (8%) | 14 (8%) | |
| | T4, TX | | 7 (3%) | 4 (5%) | 3 (2%) | |
| Prior Chemo Treatment | No | | 148 (59%) | 49 (59%) | 99 (60%) | 0.96 |
| | Yes | | 101 (41%) | 34 (41%) | 67 (40%) | |
| Prior Radiation Treatment | No | | 150 (60%) | 49 (59%) | 101 (61%) | 0.89 |
| | Yes | | 99 (40%) | 34 (41%) | 65 (39%) | |
| Treatment Arm | Letrozole | | 122 (49%) | 31 (37%) | 91 (55%) | 0.01 |
| | Placebo | | 127 (51%) | 52 (63%) | 75 (45%) | |

Real-Time RT-PCR Assays for H/I and MGI

Primer and probe sequences for HOXB13 and IL17BR, as well as control genes ESR1, PGR, CHDH, ACTB, HMBS, SDHA and UBC, were used as described previously (Ma et al., supra). Primer and probe sequences for the five molecular grade genes (BUB1B, CENPA, NEK2, RACGAP1 and RRM2) as well as ERBB2 (HER2) were prepared using Primer Express (ABI).

Sections of each FFPE sample were used for RNA extraction. Gross macro-dissection was used to enrich for tumor content. RNA extraction, reverse transcription, and TaqMan RT-PCR using the ABI 7900HT instrument (Applied Biosystem, Inc) were performed as described before (Ma et al., id.). The cycling threshold numbers (CTs) were normalized to the mean CT of four reference genes (ACTB, HMBS, SDHA and UBC). The use of these genes is supported by the previous reports regarding these genes and representative sequences of each of these genes known to the skilled person. Normalized CTs were taken to represent relative gene expression levels.

Calculation of H/I and MGI

Generally, and with respect to MGI, it is preferred that the expression levels of the disclosed genes are combined to form a single index that serves as a strong prognostic factor and predictor of clinical outcome(s). The index is a summation of the expression levels of the genes used and uses coefficients determined from principle component analysis to combine cases of more than one disclosed gene into a single index. The coefficients are determined by factors such as the standard deviation of each gene's expression levels across a representative dataset, and the expression value for each gene in each sample. The representative dataset is quality controlled based upon the average expression values for reference gene(s) as disclosed herein.

Stated differently, and with respect to MGI, normalized expression levels for the five genes from microarrays or RT-PCR were standardized to mean of 0 and standard deviation of 1 across samples within each dataset and then combined into a single index per sample via principle component analysis (PCA) using the first principle component. Standardization of the primary expression data within each dataset was necessary to account for the different platforms (microarrays and RT-PCR) and sample types (frozen and FFPE). As a result, and following scaling parameters, a formula for the summation of expression values that defines the index is generated. The precision of the scaling parameters can then be tested based on the means, standard errors, and standard deviations (with confidence intervals) of the expression levels of the genes across the data set. Therefore, generation of the formula for the index is dependent upon the dataset, reference gene, and genes of the MGI.

The HOXB13:IL17BR ratio was calculated as the difference in standardized expression levels between HOXB13 and IL17BR as described previously (Ma et al., id.). The means and standard deviations for HOXB13 and IL17BR used for standardizing the Table 1 cohort may be derived from an analysis of 190 FFPE tissue sections from a separate population-based cohort of estrogen receptor-positive lymph node-negative breast cancer patients.

For MGI, obviously abnormal raw $C_T$ values were removed prior to averaging the values over duplicates for each gene and each sample. The averaged raw $C_T$ value for each gene was then normalized by the averaged $C_T$ value of four reference genes (ACTB, HMBS, SDHA, and UBC). The normalized expression levels ($\Delta C_T$) for the five genes were combined into a single index per sample, which can be compared to a pre-determined cutoff value, such as 0, where high MGI is above the cutoff and low MGI is below the cutoff.

Continous BCI

A continuous risk model was built by combining H:I and MGI as continuous variables. The linearity of these two variables were checked by fitting a Cox proportional hazard regression model with restricted cubic splines, and H:I demonstrated significant non-linearity. A polynomial function of H:I was used to approximate the restricted models using Akaike Information Criterion. The resulting predictor from the final Cox regression model was then re-scaled into the range of 0 to 10, which is referred to as the BCI.

The BCI is further categorized into three levels: low risk, BCI<5; intermediate risk, 5≤BCI<6.4; high risk, BCI>6.4.

These cut-offs were chosen such that the resulting proportions of low, intermediate, and high risk groups were similar to those formed by the three categorical combination groups of H:I and MGI.

Cut-Points and Statistical Analyses

H/I CUT-POINT: The cutpoint of 0.06 for the HOXB13: IL17BR ratio, previously defined to stratify patients treated with adjuvant tamoxifen into low and high risk of recurrence, may be used in this study.

MGI CUT-POINT: The calculation and the cutpoint for MGI were defined without using any clinical outcome data and instead was a natural cutpoint. Initial analysis of MGI in the Uppsala cohort indicated good discrimination of grade 1 and grade 3 tumors using the mean (0) as cutpoint, and model-based clustering of MGI also indicated a bimodal distribution with a natural cutpoint around 0. This cutpoint was further supported by receiver operating characteristic (ROC) analysis.

STATISTICAL ANALYSES: Kaplan-Meier analysis with logrank test and Cox proportional hazards regression were performed to assess the association of gene expression indexes with clinical outcome. Multivariate Cox regression models were performed to assess the prognostic capacity of gene expression indexes after adjusting for known prognostic factors.

Proportional hazards (PH) assumption was checked by scaled Schoenfeld residuals; variables violating PH assumption were adjusted for in the model through stratification. To account for the case-cohort design of the Table 1 cohort, we used weighted Kaplan-Meier analysis and Cox regression models with modifications to handle case-cohort designs (see [19,20] as implemented in the survey package in R (www.r-project.org). To test for interaction between dichotomized MGI and the H:I ratio in Cox regression models, the Wald statistic was used in the Table 1 cohort and likelihood ratio test was used in the last cohort.

Correlations of continuous variables with categorical factors were examined using non-parametric two-sample Wilcoxon test or Kruskal-Wallis test for factors with more than two levels.

All statistical analyses were performed in the R statistical environment. All significance test were two-sided, and p<0.05 was considered significant.

Example II: Prognostic Performance

Table 2 shows the distribution of the cases and controls to the continuous BCI risk groups.

TABLE 2

| BCI group, (%) | Cases (n = 83) | Controls (n = 166) |
|---|---|---|
| Low | 43.4% | 57.8% |
| Intermediate | 22.9% | 18.1% |
| High | 33.7% | 24.1% |

Table 3 shows the univariate analysis in relation to cancer recurrence in MA.17 subjects.

TABLE 3

Univariate analysis in relation to cancer recurrence

| | Odds Ratio (95% CI) | P-value |
|---|---|---|
| Treatment (Placebo vs Letrozole) | 2.02 (1.17-3.47) | 0.01 |
| Tumor Grade | | 0.28 |
| II vs. I | 1.73 (0.61-4.88) | 0.30 |
| III vs. I | 2.53 (0.81-7.90) | 0.11 |
| Analysis of BCI | | |
| BCI | 2.38 (1.21-4.69) | 0.01 |
| BCI, High vs Low | 1.87 (1.00-3.50) | 0.05 |
| Analysis of components of BCI | | |
| HoxB13 | 1.34 (1.05-1.70) | 0.02 |
| HoxB13, High vs Low | 2.17 (1.27-3.69) | 0.004 |
| H:I | 2.52 (1.08-5.85) | 0.03 |
| H:I, High vs Low | 1.68 (1.00-2.81) | 0.049 |
| MGI | 1.83 (0.93-3.58) | 0.08 |
| MGI, High vs Low | 1.49 (0.87-2.56) | 0.15 |

Table 4 shows multivariate analysis in relation to cancer recurrence

TABLE 4

Multivariate analysis in relation to cancer recurrence

| | Odds Ratio (95% CI) | P-value |
|---|---|---|
| Analysis with BCI | | |
| BCI | 2.37 (1.08-5.22) | 0.03 |
| BCI, High vs Low | 1.87 (0.88-3.95) | 0.10 |
| Analysis with components of BCI | | |
| HoxB13 | 1.35 (1.05-1.74) | 0.02 |
| HoxB13, High vs Low | 2.32 (1.32-4.10) | 0.004 |
| H:I | 2.55 (1.03-6.32) | 0.04 |
| H:I, High vs Low | 1.71 (0.98-2.97) | 0.06 |
| MGI | 1.61 (0.73-3.54) | 0.24 |
| MGI, High vs Low | 1.37 (0.73-2.55) | 0.33 |

As shown by the above, BCI is prognostic of late cancer recurrences in ER+ patients following 5 years of tamoxifen treatment. HoxB13 expression is also prognostic of late cancer recurrences in ER+ patients following 5 years of tamoxifen treatment.

Example III: Biomarker and Treatment Interaction

Table 5 shows interactions between the gene expression analyzed and treatment.

TABLE 5

Biomarker and Treatment Interaction

| | P-value |
|---|---|
| HoxB13 | 0.047 |
| H:I | 0.97 |
| MGI | 0.06 |
| BCI | 0.42 |
| BCI High vs Intermediate + Low | 0.08 |

Table 6 shows the distribution of HoxB13 gene expression in relation to treatments used. HoxB13 expression at diagnosis predicts patient benefit from extended endocrine therapy with letrozole after 5 years of adjuvant tamoxifen therapy.

TABLE 6

| | Letrozole | | Placebo | | |
| --- | --- | --- | --- | --- | --- |
| | Controls | Cases | Controls | Cases | P-value |
| Low HoxB13 | 48 | 14 (23%) | 46 | 16 (26%) | 0.83 |
| High HoxB13 | 43 | 17 (28%) | 29 | 36 (55%) | 0.004 |

BIBLIOGRAPHY

1. Ma et al., *Cancer Cell*, 5:607-16 (2004)
2. Ma et al., *J. Clin. Oncol.*, 24:4611-9 (2006)
3. Goetz et al., *Clin. Cancer Res.*, 12:2080-7 (2006)
4. Jerevall et al., *Breast Cancer Res. Treat* (2007)
5. Jansen et al., *J. Clin. Oncol.* 25:662-8 (2007)
6. Cianfrocca et al., *Oncologist*, 9:606-16 (2004)
7. Sotiriou et al., *J. Natl. Cancer Inst.*, 98:262-72 (2006)
8. van't Veer et al., *Nature*, 415:530-6 (2002)
9. Paik et al., *N. Engl. J. Med.*, 351:2817-26 (2004)
10. Desmedt et al., *Cell Cycle*, 5:2198-202 (2006)
11. Loi et al. *J. Clin. Oncol.*, 25:1239-46 (2007)
12. Sotiriou et al., *Nat. Rev. Cancer*, 7:545-53 (2007)
13. Miller et al., *Proc. Natl. Acad. Sci. USA*, 102:13550-5 (2005)
14. Pawitan et al., *Breast Cancer Res.* 7:R953-64 (2005)
15. Rundle et al., *Cancer Epidemiol Biomarkers Prev.*, 14:1899-907 (2005)
16. Ma et al., *Proc. Natl. Acad. Sci. USA*, 100:5974-9 (2003)
17. Whitfield et al., *Mol. Biol. Cell*, 13:1977-2000 (2002)
18. Hirose et al., *J. Biol. Chem.*, 276:5821-5828 (2001)
19. Goldhirsch et al., *Ann. Oncol.*, 16:1569-83 (2005)

All references cited herein, including patents, patent applications, and publications, are hereby incorporated by reference in their entireties, whether previously specifically incorporated or not.

Having now fully described the inventive subject matter, it will be appreciated by those skilled in the art that the same can be performed within a wide range of equivalent parameters, concentrations, and conditions without departing from the spirit and scope of the disclosure and without undue experimentation.

While this disclosure has been described in connection with specific embodiments thereof, it will be understood that it is capable of further modifications. This application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth.

What is claimed is:

1. A method of treating breast cancer in a subject who has undergone removal of estrogen receptor positive (ER+) breast cancer and has been treated with a first endocrine therapy of a selective estrogen receptor modulator (SERM), a selective estrogen receptor down-regulator (SERD), or an aromatase inhibitor (AI), the method comprising:
   preparing cDNA from nucleic acids in a sample of ER+ breast cancer cells from the subject,
   measuring the expression level of the HoxB13, IL17BR, Bub1B, CENPA, NEK2, RACGAP1, and RRM2 genes from said cDNA,
   calculating a ratio of expression levels of HoxB13:IL17BR ("H:I ratio") using the subject's expression levels,
   calculating a molecular grade index ("MGI") comprising summing expression levels of Bub1B, CENPA, NEK2, RACGAP1, and RRM2 using the subject's expression levels,
   building a continuous risk model by combining an H:I ratio and a MGI as continuous variables from a plurality of reference patients,
   establishing a reference breast cancer index (BCI) value for ER+ breast cancer patients that did not have cancer recurrence and/or ER+ breast cancer patients that did have cancer recurrence by combining the H:I ratio and MGI from the plurality of reference patients, wherein the reference BCI value has a cut-off value greater than 6.4,
   calculating the subject's BCI value by combining the subject's H:I ratio and MGI,
   comparing the subject's BCI value to the cut-off value,
   classifying the subject as having recurrence of breast cancer if the subject's BCI value is (a) above 6.4 for the patients that did not have cancer recurrence and/or (b) not below 6.4 for the patients that did have cancer recurrence, wherein risk of cancer recurrence is higher above the cut-off than below the cut-off, and
   treating the subject classified as having a high risk of recurrence with a second endocrine therapy.

2. The method of claim 1, wherein said second endocrine therapy is different from the first endocrine therapy.

3. The method of claim 2, wherein said first endocrine therapy is tamoxifen and the second endocrine therapy is letrozole, or wherein the first endocrine therapy is letrozole and the second endocrine therapy is tamoxifen.

4. The method of claim 1, wherein said second endocrine therapy comprises a SERM, a SERD or an AI.

5. The method of claim 1, wherein said second endocrine therapy is a SERM, a SERD or an AI.

6. The method of claim 1, wherein said first endocrine therapy is for about five years.

7. The method of claim 1, wherein said patient is a pre-menopausal woman or a post-menopausal woman.

8. The method of claim 1 wherein said cancer is ductal carcinoma in situ (DCIS) and said cancer recurrence comprises local recurrence.

9. The method of claim 1, wherein said treating comprises treating the subject with a different second endocrine therapy after cessation of treatment with the first endocrine therapy based on classifying the subject as expected to benefit from a change in treatment.

10. The method of claim 1, wherein the continuous risk model is a Cox regression model.

11. The method of claim 1, wherein said nucleic acids are mRNA from said sample, and said measuring comprises nucleic acid amplification.

12. The method of claim 1, wherein said measuring comprises using an array.

13. The method of claim 1, wherein said sample is dissected from tissue removed from said subject.

14. The method of claim 1, wherein said sample of ER+ breast cancer cells comprises fresh tissue, freshly frozen tissue, or fixed tissue.

15. The method of claim 14, wherein said sample is a formalin fixed paraffin embedded (FFPE) sample.

* * * * *